United States Patent
Falla et al.

(10) Patent No.: US 9,511,042 B2
(45) Date of Patent: Dec. 6, 2016

(54) N-ACYL AMINO ACID DERIVATIVES FOR TREATING SKIN CONDITIONS SUCH AS CELLULITE

(75) Inventors: Timothy J. Falla, Woodinville, WA (US); Lijuan Zhang, Kenmore, WA (US)

(73) Assignee: HELIX BIOMEDIX INC., Bothell, WA (US)

( * ) Notice: Subject to any disclaimer, the term of this patent is extended or adjusted under 35 U.S.C. 154(b) by 64 days.

(21) Appl. No.: 13/703,292

(22) PCT Filed: Jun. 28, 2011

(86) PCT No.: PCT/US2011/042123
§ 371 (c)(1),
(2), (4) Date: Dec. 10, 2012

(87) PCT Pub. No.: WO2012/003176
PCT Pub. Date: Jan. 5, 2012

(65) Prior Publication Data
US 2013/0096143 A1    Apr. 18, 2013

Related U.S. Application Data

(60) Provisional application No. 61/361,179, filed on Jul. 2, 2010.

(51) Int. Cl.
| | | |
|---|---|---|
| *A61K 8/44* | (2006.01) | |
| *A61K 8/42* | (2006.01) | |
| *C07C 237/12* | (2006.01) | |
| *A61K 31/198* | (2006.01) | |
| *A61K 31/20* | (2006.01) | |
| *A61Q 19/06* | (2006.01) | |
| *A61K 45/06* | (2006.01) | |

(52) U.S. Cl.
CPC ............... *A61K 31/198* (2013.01); *A61K 8/42* (2013.01); *A61K 8/44* (2013.01); *A61K 31/20* (2013.01); *A61K 45/06* (2013.01); *A61Q 19/06* (2013.01); *C07C 237/12* (2013.01)

(58) Field of Classification Search
CPC .......................... C07C 237/07; C07C 237/12
See application file for complete search history.

(56) References Cited

U.S. PATENT DOCUMENTS

| 5,510,531 A | 4/1996 | Higuchi et al. |
|---|---|---|
| 2003/0018081 A1 | 1/2003 | Piomelli et al. |
| 2005/0019372 A1 | 1/2005 | Corkey et al. |

FOREIGN PATENT DOCUMENTS

| EP | 0500332 A2 | | 8/1992 |
|---|---|---|---|
| EP | 1938789 | * | 7/2008 |
| JP | H02-268145 A | | 11/1990 |
| JP | 08-337515 | | 12/1996 |
| JP | 2005-194252 | | 7/2005 |
| JP | 2006183039 | * | 7/2006 |
| JP | 2007-153845 | | 6/2007 |
| JP | 2007-314464 A | | 12/2007 |
| RU | 2245358 C2 | | 1/2005 |
| WO | 90/14429 A1 | | 11/1990 |
| WO | 2004/069240 A2 | | 8/2004 |
| WO | 2006/029818 A2 | | 3/2006 |
| WO | WO2006029818 | * | 3/2006 |
| WO | 2006/082978 A1 | | 8/2006 |

OTHER PUBLICATIONS

Kono, Mitsuyoshi et al. JP2006183039. Jul. 2006. Machine Translation.*
Caruso et al. (Journal of Plastic, Reconstructive & Aesthetic Surgery (2008) 61, 1321-1324).*
Thomas et al. EP1938789. Jul. 2008.*
Patani et al. (Chemical Reviews, 1996, vol. 96, No. 8).*
Enzo Emanuele, M.D. (Cellulite: Advances in treatment: Facts and controversies. Clinics in Dermatology (2013) 31, 725-730).*
See Luebberding et al. Cellulite: An Evidence-Based Review. Am J Clin Dermatol (2015) 16:243-256.*
Notification of Transmittal of the International Search Report and The Written Opinion of the International Searching Authority, or the Declaration, dated Aug. 24, 2011, 16 pages.
Article from Nutrition & Metabolism, Biomed Central; by Guo Wen et al., entitled "Modulation of Adipocyte Lipogenesis by Octanoate: Involvement of Reactive Oxygen Species"; vol. 3, No. 1, Jul. 27, 2006; 8 pages.
Article from Tetrahedron Letters, by Jin Zhuang et al., entitled "Copper Mediated Oxidation of Amides to Imides by Selectfluor"; vol. 52, No. 16, Apr. 20, 2011, pp. 1956-1959.
Fujimoto, Y., et al., 2006. Long Chain fatty acids induce lipid droplet formation in a cultured human hepatocyte in a manner deopendent of acyl-CoA synthesis. Biol. Pharm. Bull. 29 (11) 2174-2180.
Guo, W., et al., 2006. Modulation of adipogensis by octanoate: involvement of reactive oxygen species. Nutrition & Metabolism 3(30) 1-8.
Han, J., et al., 2002. Octanoate attenuates adipogenesis in 3T3-preadipocytes. J. Nutr. 132:904-910.
pubchem.ncbi.nim.nih.gov/summary/summary.cgi?sid=4728815.
pubchem.ncbi.nim.nih.gov/summary/summary.cgi?sid=37555064.
pubchem.ncbi.nim.nih.gov/summary/summary.cgi?sid=75064649.
New Zealand Examination Report dated Dec. 11, 2013, relating to New Zealand Application No. 605804.
Kawase, Tokuzo et al., "A Novel Synthesis of N-Alkoxycarbonyl Amino Acids and Surfactant Properties of Their Sodium Salts," Journal of Oleo Science, 59, (4) 191-201 (2010).

(Continued)

*Primary Examiner* — Jeffrey S Lundgren
*Assistant Examiner* — Chris Simmons
(74) *Attorney, Agent, or Firm* — Thomas Law PLLC

(57) ABSTRACT

The invention relates to small molecules having biological and therapeutic activity. Particularly, the invention relates to small molecules having lipolytic and anti-adipogenic activity. Two examples of such molecules are 4-methyl-2-(octanoylamino) pentanoic acid and N-isopentyloctanamide. The invention further relates to methods of preventing or treating skin conditions such as cellulite using small molecules having lipolytic and anti-adipogenic activity.

20 Claims, 6 Drawing Sheets

(56) References Cited

OTHER PUBLICATIONS

Sivagnanam, G. Mesotherapy—The french connection. J Pharmacol Pharmacother [serial online] 2010 [cited Dec. 10, 2015];1:4-8. Available from: http://www.jpharmacol.com/text.asp?2010/1/1/4/64529.
Caruso, M.K. et al.,An evaluation of mesotherapy solutions for inducing lipolysis and treating cellulite,J Plast Reconstr Aesthet Surg (2007), doi:10.1016/j.bjps.2007.03.039.
RU2013104424, "Official Action," mailed Feb. 2, 2016, 6 pgaes.
PH1-2012-502423, "Substantive Examination Report," mailed Mar. 31, 2016, 2 pages.
RU2013104424, "Decision of Grant," mailed Apr. 22, 2016, 14 pages.
KR10-2013-7001965, "Decision for Patent Grant," mailed Jun. 14, 2016, 3 pages.
JP2013-518561, "Notice of Reasons for Refusal," mailed Feb. 2, 2016, 7 pages.
Zhang, et al., "Effect of Amide Constituents from Pepper on Adipogenesis in 3T3-L1 Cells," Bioorganic & Medicinal Chemistry Letters 18 (2008), pp. 3272-3277.
Isopentyl caprylamide, RN: 546098-90-2. Datasheet [online] Toxnet, 2003 [retrieved on Sep. 15, 2016]. Retrieved from the Internet: <URL: https://chem.nlm.nih.gov/chemidplus/rn/546098-90-2> 1 page.
JP2013-518561, Notice of Reasons for Refusal, mailed Aug. 30, 2016, 5 pages.
PH1/2012/502423, Subsequent Substantive Examination Report, mailed Aug. 18, 2016, 2 pages.

\* cited by examiner

A

4-Methyl-2-(octanoylamino) pentanoic acid

$C_{14}H_{27}NO_3$    MW=257

B

N-isopentyloctanamide

$C_{13}H_{27}NO$    MW=213

N-ACYL AMINO ACID DERIVATIVES FOR TREATING SKIN CONDITIONS SUCH AS CELLULITE

This application is a Section 371, United Stated national stage filing of PCT/US2011/042123 filed 28 Jun. 2011 which claims benefit of priority to U.S. 61/361,179, filed 2 Jul. 2010, each of which is herein incorporated by reference in its entirety.

FIELD OF THE INVENTION

The invention relates to small molecules having biological and therapeutic activity. Particularly, the invention relates to small molecules having lipolytic and anti-adipogenic activity. Two examples of such molecules are 4-methyl-2-(octanoylamino) pentanoic acid and N-isopentyloctanamide. The invention further relates to methods of preventing or treating skin conditions such as cellulite using small molecules having lipolytic and anti-adipogenic activity.

BACKGROUND OF THE INVENTION

Cellulite can result from the accumulation of degraded fatty tissue in the skin. One or several factors contributing to this disorder include poor arterial or venous circulation, hormonal disturbances and problems with lymphatic drainage. One condition underlying cellulite production is excessive fat storage in skin adipocytes. By becoming heavily laden with fat (lipids in the form of triglycerides), the adipocytes swell and become hypertrophic, sometimes to a high degree. The compression of the blood and lymph vessels by the fatty masses resulting from the hypertrophy induces poor fluid drainage and stagnation of the toxins in the skin. The edema and degeneration of connective tissue resulting from these conditions lead to the irregular stippled appearance that characterizes cellulite.

One of the goals of the skin care industry is to develop small (less than 500 MW) molecules capable of skin penetration that can stimulate the breakdown of fat deposits in cellulite and other abnormalities of the skin. It has been demonstrated that octanoic acid, a free fatty acid that is also referred to as octanoate or caprylic acid, is involved in the body's natural modulation of lipid metabolism in adipocytes (2000, Guo et al., *Biochem. J.* 349:463-471; 2002, Han et al., *J. Nutr.* 132:904-910; 2004, Lei et al., *Obesity Res.* 12:599-610; 2006, Guo et al., *Nutr. Metab.* (*Lond.*) 3:30; U.S. Pat. Appl. Publ. No. 2005/0019372), and therefore is a candidate drug for treating cellulite. Octanoic acid is naturally found in milk and some plant oils (e.g., coconut and palm), and is a widely used dietary supplement taken for a broad range of purposes including anti-fungal activity. Aside from its lipolytic activity, octanoic acid is also taken up by adipocytes and used along with glycerol and other fatty acid to synthesize triglycerides (FIG. 1).

Other compounds besides octanoic acid known to modulate lipid metabolism in adipocytes are primarily adapted from systemic drugs that have been developed for various heart and respiratory conditions. These include isoproterenol (a beta-adrenergic agonist), aminophylline (a phosphodiesterase inhibitor) and theophylline (a phosphodiesterase inhibitor similar in structure to caffeine). These molecules are injected as part of a mesotherapy regimen or used topically for effecting fat reduction in conditions such as cellulite deposition. To improve upon the availability of molecules such as these for application to skin care products would require producing agents that (i) are non-prescription drugs, (ii) are more natural in origin, (iii) exhibit good skin penetration qualities, and (iv) have increased lipolytic activity over the currently available molecules.

SUMMARY OF THE INVENTION

An embodiment of the instant invention can be directed to a method of treating the skin of a mammal, comprising administering to the skin of a mammal a composition. The composition may comprise a pharmaceutically acceptable carrier and a pharmaceutically effective amount of a compound or its pharmaceutically acceptable salt. The compound in turn may comprise the formula $R_1$—C(O)—NH—$R_2$ where $R_1$ comprises a chain of 5 to 35 carbon atoms, the $R_1$—C(O) portion of the formula is a fatty acyl group, and $R_2$ comprises an organic group.

In certain embodiments of the invention, the NH—$R_2$ portion of the $R_1$—C(O)—NH—$R_2$ formula may comprise an amino acid. In this case the $R_2$ group comprises the alpha-carbon, carboxyl group and side group of the amino acid; the NH group is linked to the alpha-carbon of the amino acid. In other embodiments of the invention, the NH—$R_2$ portion of the $R_1$—C(O)—NH—$R_2$ formula may comprise an analog of an amino acid, in which case the analog differs from the amino acid by lacking the carboxylic group linked to the amino acid alpha-carbon. In this case, the $R_2$ group comprises the alpha-carbon and side group of the amino acid; the NH group is linked to the alpha-carbon of amino acid analog. The side group of the amino acid or amino acid analog may be hydrophobic. The amino acid in these embodiments (either full amino acid or the above analog) may be leucine, isoleucine, valine, or alanine.

Certain embodiments of the above method employ a compound comprising or consisting of the formula:

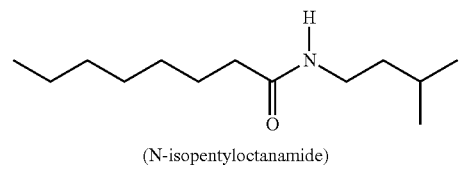

(N-isopentyloctanamide)

Certain other embodiments of the above method employ a compound comprising or consisting of the formula:

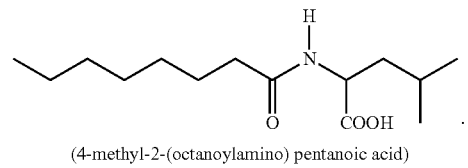 [SMILES: CCCCCCCC(=O)NC(CC(C)C)C(=O)O]

(4-methyl-2-(octanoylamino) pentanoic acid)

In the 4-methyl-2-(octanoylamino) pentanoic acid embodiment, it is apparent that the $R_2$ group is a leucine, whereas the $R_2$ group in the N-isopentyloctanamide embodiment is a leucine lacking the carboxyl group. Embodiments further include the pharmaceucally acceptable salts of the subject compounds.

In certain embodiments of the invention, the chain of the $R_1$ group of the $R_1$—C(O)—NH—$R_2$ formula may comprise 7 to 21 carbon atoms. In these and other embodiments, where the $R_1$ chain is 7 carbon atoms in length, the fatty acyl group $R_1$—C(O)— would be an octanoyl group. These and other embodiments of the invention may comprise an $R_2$ group that comprises 2 to 15 carbon atoms; such an $R_2$ group may optionally consist of carbon and hydrogen atoms. Still in other embodiments of the invention, the $R_2$ can comprise 5 to 9 carbon atoms and the $R_1$ group can comprise 5 to 13 carbon atoms. The fatty acyl group in one or more embodiments of the invention can be saturated or unsaturated.

The composition used in certain embodiments of the above method can be in the form of an aerosol, emulsion, liquid, lotion, cream, paste, ointment, powder, or foam. In addition to comprising a compound having the formula $R_1$—C(O)—NH—$R_2$, the composition may further comprise carnitine, resveratrol, isoproterenol, aminophylline, theophylline, caffeine or any other lypolysis-inducing agent or lipogenesis-inhibiting agent.

In certain embodiments of the above method, the compound may be administered to skin over a subcutaneous layer that comprises a distribution of fat that is abnormal with respect to normal subcutaneous tissue. In other embodiments, the compound may be administered to skin over a subcutaneous layer that is prone to developing a distribution of fat that is abnormal with respect to normal subcutaneous tissue. Certain embodiments of the invention comprise administering the compound to skin comprising cellulite or to skin that is prone to developing cellulite.

Embodiments of the invention are also drawn to a method of increasing glycerol production by a cell that comprises contacting said cell with a compound comprising the formula $R_1$—C(O)—NH—$R_2$, where $R_1$ comprises a chain of 5 to 35 carbon atoms, the $R_1$—C(O) portion of the formula is a fatty acyl group, and $R_2$ comprises an organic group. In certain embodiments, the cell targeted by this method is an adipocyte, or an adipocyte comprised in subcutaneous adipose tissue. With certain embodiments, the compound causes the cell to metabolize triglyceride molecules stored in the cell to glycerol and fatty acids.

Embodiments of the invention are also drawn to a method of reducing adipogenesis that comprises contacting a cell with a compound comprising the formula $R_1$—C(O)—NH—$R_2$, where $R_1$ comprises a chain of 5 to 35 carbon atoms, the $R_1$—C(O) portion of the formula is a fatty acyl group, and $R_2$ comprises an organic group. In certain embodiments, the cell targeted by this method is an adipocyte or pre-adipocyte, or an adipocyte or pre-adipocyte comprised in subcutaneous tissue. With certain embodiments, the compound causes the cell (e.g., adipocyte or pre-adipocyte) to reduce lipid accumulation. Reduced lipid accumulation can be a decrease in cytoplasmic lipids.

DETAILED DESCRIPTION OF THE INVENTION

Figure 1:
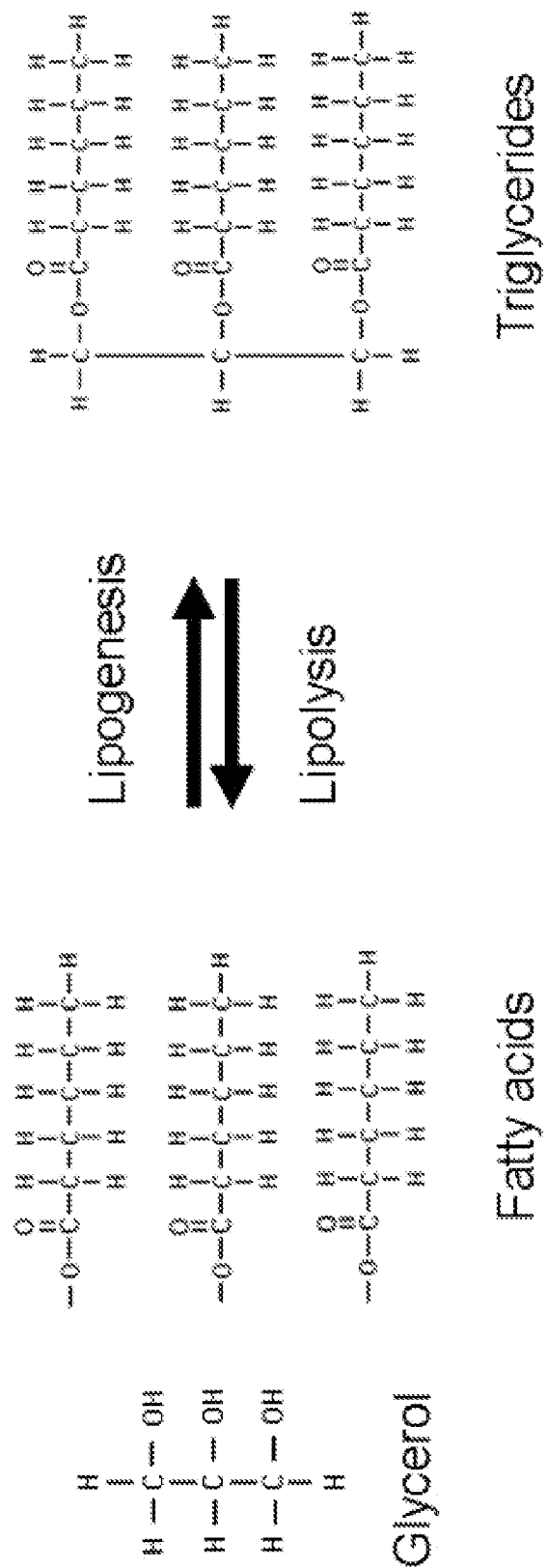
FIG. 1 shows the metabolic processes for lipogenesis and lipolysis. The depicted fatty acids are hexanoic acid molecules.

The instant invention provides compounds, fatty amides in particular, for modulating adipocytes such as through the stimulation of lipolytic processes. Examples of these compounds are 4-methyl-2-(octanoylamino) pentanoic acid (FIG. 2A) and N-isopentyloctanamide (FIG. 2B), which are each less than 300 MW and induce the breakdown of triglycerides in adipocytes to a greater extent than currently available molecules such as isoproterenol, aminophylline and theophylline. These compounds are disclosed herein to lack toxicity toward skin cells. These features, along with their being lipidated which renders them capable of penetrating the skin, make these compounds particularly useful for preventing and treating the negative effects of abnormal adipose deposition in the skin (e.g., cellulite and stretch marks). This beneficial effect of the instant invention on the skin is also associated with an enhancement of glycerol levels in the skin, which enhances skin condition.

An example compound of the instant invention is 4-methyl-2-(octanoylamino) pentanoic acid. This compound is alternatively referred to as 4-methyl-2-(capryloylamino) pentanoic acid, 4-methyl-2-(octanoylamino) valeric acid, or 4-methyl-2-(capryloylamino) valeric acid, for example. The nomenclature for this molecule is based on there being an octanoylamino group at carbon position 2 (position 1 being the carboxylic acid group carbon) of the pentanoic acid and a methyl group at carbon position 4 of the pentanoic acid. Compounds comprising or consisting of 4-methyl-2-(octanoylamino) pentanoic acid can be used in the instant invention.

Another example compound of the instant invention is N-isopentyloctanamide. This compound is alternatively referred to as N-isoamyloctanamide, N-isopentylcaprylamide, or N-isoamylcaprylamide, for example. Compounds comprising or consisting of N-isopentyloctanamide can be used in the instant invention.

Examples of compounds that can be used the instant invention comprise or consist of the chemical formula:

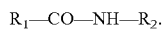
$R_1$—CO—NH—$R_2$.

The compounds 4-methyl-2-(octanoylamino) pentanoic acid and N-isopentyloctanamide follow this formula.

It is well understood in the art that the $R_1$—CO— component of formula $R_1$—CO—NH—$R_2$ can be derived from a fatty acid, for example. A skilled artisan would recognize that, since $R_1$—CO— can be derived from a fatty acid (FA), $R_1$ can comprise a hydrocarbon chain (e.g., alkane, alkene, alkyne, or variations of FA chains as disclosed herein) and —CO— can be from a carboxylic acid group that has condensed with the —NH—R2 portion. The $R_1$—CO— component in this case would comprise or consist of a fatty acyl group. $R_1$ can be an aliphatic group comprised entirely of carbon and hydrogen, or can further comprise other atoms such as oxygen and nitrogen, for example. Examples of saturated fatty acids (i.e., where $R_1$ is an alkane) that can be used to provide the $R_1$—CO— component of the compounds of the invention have the general formula $CH_3(CH_2)_n COOH$ and are listed in Table 1.

TABLE 1

Saturated fatty acids.

| Systematic name | Common name | Shorthand designation |
| --- | --- | --- |
| butanoic acid | butyric acid | 4:0 |
| pentanoic acid | valeric acid | 5:0 |
| hexanoic acid | caproic acid | 6:0 |
| octanoic acid | caprylic acid | 8:0 |
| nonanoic acid | pelargonic acid | 9:0 |
| decanoic acid | capric acid | 10:0 |
| dodecanoic acid | lauric acid | 12:0 |
| tetradecanoic acid | myristic acid | 14:0 |
| hexadecanoic acid | palmitic acid | 16:0 |
| heptadecanoic acid | margaric (daturic) acid | 17:0 |
| octadecanoic acid | stearic acid | 18:0 |
| eicosanoic acid | arachidic acid | 20:0 |
| docosanoic acid | behenic acid | 22:0 |
| tetracosanoic acid | lignoceric acid | 24:0 |
| hexacosanoic acid | cerotic acid | 26:0 |
| heptacosanoic acid | carboceric acid | 27:0 |
| octacosanoic acid | montanic acid | 28:0 |
| triacontanoic acid | melissic acid | 30:0 |
| dotriacontanoic acid | lacceroic acid | 32:0 |
| tritriacontanoic acid | ceromelissic (psyllic) acid | 33:0 |
| tetratriacontanoic acid | geddic acid | 34:0 |
| pentatriacontanoic acid | ceroplastic acid | 35:0 |

The hydrocarbon chain of a fatty acid or fatty acyl group (i.e., $R_1$—CO—) (note that the carboxylic group carbon atom is considered as one carbon in the chain), is equal to or greater than 4 carbon atoms in length. Example fatty acids/fatty acyl groups useful in providing and/or describing the invention have chain lengths of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 carbons. It therefore follows that $R_1$ can have a chain length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 carbons. In certain embodiments, the fatty acyl group chain length is 6 to 36, 8 to 16, 8 to 18, 8 to 20, 8 to 22, or 8 to 24 carbons in length; therefore, R1 for these embodiments has a chain of 5 to 35, 7 to 15, 7 to 17, 7 to 19, 7 to 21, or 7 to 23 carbons, respectively. Other fatty acids/fatty acyl groups useful in the invention have chain lengths of an even or odd number of carbons. Short-chain, medium-chain, and long-chain fatty acids or fatty acyl groups can be used in preparing embodiments of the invention. Medium-chain fatty acids typically have from 8 (or 6) to 10 (or 12) carbon atoms, whereas long-chain fatty acids typically have 14 (or 12) and more carbon atoms. Essential and non-essential fatty acids are also part of the invention, as well as naturally derived and synthetically derived fatty acids.

Skilled artisans would know the corresponding fatty acyl group for any fatty acid; for example, the fatty acyl group for the fatty acid $CH_3(CH_2)_6 COOH$ (octanoic acid) is $CH_3(CH_2)_6 CO$— (octanoyl group) ($R_1$=7). Therefore, the description herein related to fatty acids equally relates to corresponding fatty acyl groups accordingly. Example fatty acyl groups are butanoyl, pentanoyl, hexanoyl, heptanoyl, octanoyl, nonanoyl, decanoyl, dodecanoyl, tetradecanoyl, hexadecanoyl, heptadecanoyl, octadecanoyl, eicosanoyl, docosanoyl, tetracosanoyl, hexacosanoyl, heptacosanoyl, octacosanoyl and triacontanoyl.

Fatty acids useful in practicing the invention can include saturated fatty acids (i.e., an alkane chain having no double bonds between carbons of the chain and having the maximum number of hydrogen atoms), and unsaturated fatty acids (i.e., an alkene or alkyne chain having at least one double and/or triple bond between carbons of the chain, respectively). Examples of unsaturated fatty acids are mono-unsaturated (MUFA) if only one double bond is present in the chain, polyenoic (or polyunsaturated fatty acids, PUFA) if the chain has two or more double bonds (e.g., methylene-interrupted, polymethylene-interrupted, conjugated dienes, allenic acids, cumulenic acids), and acetylenic if the chain contains a triple bond. Other examples of unsaturated fatty acids are omega-3 (n-3), omega-6 (n-6), and omega-9 (n-9) fatty acids. Examples of unsaturated fatty acids (i.e., $R_1$ is an alkene or alkyne) that can be used to provide the $R_1$—CO— component of the compounds of the invention are listed in Table 2.

TABLE 2

Unsaturated fatty acids.

| Systematic name | Common name | Shorthand designation |
| --- | --- | --- |
| 9-cis-tetradecenoic acid | Myristoleic acid | 14:1 (n-5) |
| 9-cis-hexadecenoic acid | Palmitoleic acid | 16:1 (n-7) |
| 6-cis-hexadecenoic acid | Sapienic acid | 16:1 (n-10) |
| all-cis-7,10,13-hexadecatrienoic acid | | 16:3 (n-3) |
| 9-cis-octadecenoic acid | Oleic acid | 18:1 (n-9) |
| all-cis-9,12-octadecadienoic acid | Linoleic acid | 18:2 (n-6) |
| all-cis-9,11-octadecadienoic acid | Conjugated linoleic acid | 18:2 (n-6) |
| all-cis-9,12,15-octadecatrienoic acid | α-Linolenic acid (ALA) | 18:3 (n-3) |
| all-cis-6,9,12-octadecatrienoic acid | γ-Linolenic acid (GLA) | 18:3 (n-6) |
| all-cis-6,9,12,15-octadecatetraenoic acid | Stearidonic acid (SDA) | 18:4 (n-3) |
| all-cis-11,14,17-eicosatrienoic acid | Eicosatrienoic acid (ETE) | 20:3 (n-3) |
| all-cis-8,11,14-eicosatetraenoic acid | Dihomo-γ-Linolenic acid (DGLA) | 20:3 (n-6) |
| all-cis-5,8,11,14-eicosatetraenoic acid | Arachidonic acid | 20:4 (n-6) |
| all-cis-8,11,14,17-eicosatetraenoic acid | Eicosatetraenoic acid (ETA) | 20:4 (n-3) |
| all-cis-5,8,11,14,17-eicosapentaenoic acid | Eicosapentaenoic acid (EPA) | 20:5 (n-3) |
| (Z)-Docos-13-enoic acid | Erucic acid | 22:1 (n-9) |
| all-cis-7,10,13,16,19-docosapentaenoic acid | Docosapentaenoic acid (DPA), | 22:5 (n-3) |

TABLE 2-continued

Unsaturated fatty acids.

| Systematic name | Common name | Shorthand designation |
| --- | --- | --- |
| all-cis-4,7,10,13,16,19-docosahexaenoic acid | Docosahexaenoic acid (DHA) | 22:6 (n-3) |
| all-cis-9,12,15,18,21-docosahexaenoic acid | Tetracosapentaenoic acid | 24:5 (n-3) |
| all-cis-6,9,12,15,18,21-tetracosenoic acid | Tetracosahexaenoic acid (Nisinic acid) | 24:6 (n-3) |

Other less common types of fatty acids can be used in preparing compounds the invention, including those that have other types of groups in their hydrocarbon chain beside methyl. Examples of non-methyl groups that can be in the chain are ether, carboxylic, ketone, ester, and aldehyde groups. Other examples of less common fatty acids are those having chains that have branch groups aside from hydrogen. Examples of alternative fatty acids that can be used in the invention are hydroxy fatty acids, dicarboxylic acids, fatty acid carbonates, divinyl ether fatty acids, sulfur containing fatty acids, fatty acid amides, methoxy and acetoxy fatty acids, keto fatty acids, aldehydic fatty acids, halogenated fatty acids (e.g., F, Cl, Br), nitrated fatty acids, branched-chain fatty acids, mono or multibranched chain fatty acids, branched methoxy fatty acids, branched hydroxy fatty acids (e.g., mycolic acid), ring containing fatty acids, cyclopropane acids, cyclobutane acids (e.g., ladderanes), cyclopentyl acids, furanoid acids, cyclohexyl and hexenyl acids, phenyl and benzoic alkanoic acids, epoxy acids, cyclic fatty peroxides, and lipoic acid.

While compounds of the instant invention can be prepared using the fatty acids described herein, other formats for preparing the compounds would be readily apparent to a skilled artisan. Therefore, where the instant disclosure describes the $R_1$—CO— component of formula $R_1$—CO—NH—$R_2$ formula in terms of fatty acids and production therefrom, such disclosure does not limit the compounds to having to be synthesized from fatty acids per se. Where other synthetic methods are applied to produce compounds of the invention, it is still useful and comprehensible to characterize the $R_1$—CO— component with respect to its fatty acid or fatty acyl group character.

It is well understood in the art that the $R_1$—CO—NH— component of formula $R_1$—CO—NH—$R_2$ can be derived from or described as a fatty amide (a.k.a. fatty acid amide or alkylamide), for example. Fatty amides can be produced by condensing a fatty acid, such as described herein, with an amine (e.g., ammonia, primary amine, secondary amine). Examples of fatty amides that can be used to provide the $R_1$—CO—NH— component of the $R_1$—CO—NH—$R_2$ formula are therefore readily apparent in view of the disclosed examples of fatty acids. A non-limiting list of fatty amides includes pentanamide (valeramide), hexanamide (caproamide), octanamide (caprylamide), nonanamide (pelargonamide), decanamide (capramide), dodecanamide (lauramide), tetradecanamide (myristamide), palmitamide, arachidamide, behenamide, stearamide, oleamide, erucamide, and recinoleamide.

Amino acids and derivatives thereof can be used in preparing the —NH—R2 portion of the $R_1$—CO—NH—$R_2$ formula of the compounds of the invention. Examples of amino acids that can be used are, in both L- and D-forms, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Other examples of amino acids are norleucine, norvaline, alpha-aminooctanoate, beta-methylphenylalanine, alpha-aminophenylacetate, ornithine, taurine, carnitine, γ-aminobutyric acid (GABA), L-DOPA (L-3,4-dihydroxyphenylalanine), hydroxyproline, selenomethionine, and selenocysteine Amino acids have a central carbon (the alpha-carbon, $C_\alpha$) that is linked to an amine group, carboxylic acid group, and a side group (R). The general structure of a free amino acid is as follows:

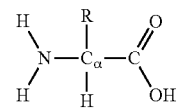

Skilled artisans would recognize that the amine group attached to the alpha-carbon of an amino acid could be used to provide the —NH portion of the $R_1$—CO—NH—$R_2$ formula, in which case $R_2$ would comprise or consist of the alpha-carbon, side group, and carboxylic group of the amino acid. An example of a compound having the $R_1$—CO—NH—$R_2$ formula with the —NH—$R_2$ portion thereof being derived from an amino acid can be 4-methyl-2-(octanoylamino) pentanoic acid:

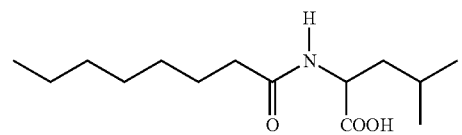 [SMILES: CCCCCCCC(=O)NC(CC(C)C)C(=O)O]

In this example, the —NH—$R_2$ portion can be derived from leucine. Alternatively, skilled artisans also recognize that the amine group as it exists in certain amino acid side groups (e.g., arginine, asparagine, glutamine, lysine, histidine, proline, tryptophan) can be used to provide the —NH portion of the $R_1$—CO—NH—$R_2$ formula, in which case $R_2$ would comprise or consist of the alpha-carbon, carboxylic group, amino group, and rest of the side group of the amino acid.

Amino acid derivatives include salt derivatives and derivatives lacking the amine group or the carboxyl group linked to the alpha-carbon. Other examples are those amino acids modified in their side group, such as by esterification or amidation. An example of a compound having the $R_1$—CO—NH—$R_2$ formula with the —NH—$R_2$ portion thereof being derived from an amino acid analog can be N-isopentyloctanamide:

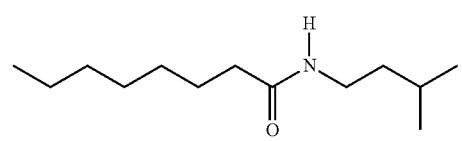

In this example, the —NH—$R_2$ portion can be derived from a leucine that lacks the carboxyl (COOH) group that is otherwise linked to the alpha-carbon.

The side group of an amino acid or amino acid derivative, for which the —NH—$R_2$ portion of the $R_1$—CO—NH—$R_2$ formula may be derived or otherwise resemble, may be positively charged, negatively charged, polar, polar uncharged, nonpolar, hydrophobic, acidic, basic, aliphatic, or neutral.

It is well understood in the art how compounds of the instant invention can be produced. For example, synthesis methods can include the condensation or linkage of a fatty acid (e.g., those described herein) with an amino acid or an amino acid-related compound. U.S. Patent Appl. Publ. No. 2008/0200704, which is incorporated herein by reference in its entirety, discloses an example of this type of organic synthesis. Also, skilled artisans would recognize how the methodology disclosed below (Examples) regarding the synthesis of 4-methyl-2-(octanoylamino) pentanoic acid and N-isopentyloctanamide could be applied for preparing other compounds for practicing the invention.

It should be apparent that where the present disclosure refers to formula segments being derived from an amino acid or any other moiety or group, such disclosure is referring to both products that were indeed produced using said amino acid, group or moiety, as well as to products produced from other components. In the latter examples, it can be useful to refer to the final product with respect to groups therein based on their similarity or matching to certain chemical groups such as amino acids.

The —NH—$R_2$ portion of the $R_1$—CO—NH—$R_2$ formula can be considered to be a cap, capping group, or blocking group to the $R_1$—CO— fatty acyl group. In this sense, the —NH—$R_2$ portion prevents the fatty acyl group from forming an ester with an alcohol group (R—OH). Since the acyl group is in amide linkage, its carboxyl carbon is not susceptible or less susceptible to nucleophilic attack by an electrophile such as an alcohol.

Examples of compounds that can be used in the instant invention are partly or entirely lipophilic (hydrophobic) and under a molecular weight of about 200, 250, 300, 350, 400, 450, 500, 550, or 600. In general, the lipophilicity of the compounds can be provided in large part by the $R_1$ group. Those compounds of the invention that are partly lipophilic can be polarized in that the $R_1$ group is of a hydrophobic character and the $R_2$ group, optionally in conjunction with the intermediary —CO—NH— core comprises some hydrophilic character. The compounds of the instant invention and/or its $R_1$ or $R_2$ components can be about 100%, 95%, 90%, 85%, 80%, 75%, 70%, 65%, 60%, 55%, 50%, 45%, 40%, 35%, or 30% lipophilic or hydrophobic.

Other examples of the instant invention are compounds that have the formula $R_1$—CO—NH—$R_2$ according to the disclosure herein and that have the same activity (e.g., lipolytic activity) as 4-methyl-2-(octanoylamino) pentanoic acid or N-isopentyloctanamide, or at least about 10%, 20%, 30%, 40%, 50%, 55%, 60%, 65%, 70%, 75%, 80%, 90%, 95%, 96%, 97%, 98%, or 99% of the activity of either of these compounds.

All of the embodiments of the compounds of the invention may be in the "isolated" state. For example, an "isolated" compound is one that has been completely or partially purified. In some instances, the isolated compound will be part of a greater composition, buffer system or reagent mix. In other circumstances, the isolated compound may be purified to homogeneity. A composition may comprise the compound at a level of at least about 50, 80, 90, or 95% (on a molar basis or weight basis) of all the other species that are also present therein. Mixtures of the disclosed compounds may be used in practicing methods provided by the invention.

Additional embodiments of the current invention are directed towards methods of using the compounds disclosed herein in formulations or as therapeutic agents, for example. These methods may involve the use of a single compound, or multiple compounds in combination (i.e., a mixture). Accordingly, certain embodiments of the invention are drawn to medicaments comprising compounds disclosed herein, and methods of manufacturing such medicaments.

In certain instances, the inventive composition can be disposed within devices placed upon, in, or under the skin. Such devices include transdermal patches, implants, and injections (e.g., mesotherapy) which release the substances in such a manner as to contact the skin or hair follicle either by passive or active release mechanisms. The substance can be applied, for example, topically to the epidermis at regular intervals, such as once or twice daily, in a suitable vehicle and at an effective concentration. One or more injections to the skin offer another route for administering the inventive peptides to the skin or any other tissue.

The compositions used to deliver compounds in the methods described herein can be in the form of an aerosol, emulsion, liquid, lotion, cream, paste, ointment, powder, foam, or other pharmaceutically acceptable formulation. Furthermore, compounds can be delivered using less involved formulations such as deionized/distilled water, PBS or standard medical saline solutions. Generally, a pharmaceutically acceptable formulation would include any carrier suitable for use on human skin or mucosal surface. Such pharmaceutically acceptable carriers include ethanol, dimethyl sulfoxide, glycerol, silica, alumina, starch, and equivalent carriers and diluents. The formulation may optionally have cosmetic appeal, and/or contain other agents such as retinoids or other peptides that can act as adjuvants for the therapeutic action of the inventive peptides. Antibiotics can also be added to the formulation in order to ward off infection, thereby permitting maximal healing processes to occur. Therapeutic and/or cosmetic peptides may be used in conjunction with the compounds of the invention. The concentration of the compound(s) in the composition can be about 0.1 µg/mL to about 50 µg/mL or about 0.1 µg/mL to about 100 µg/mL; however, the ultimate concentration employed may vary outside these ranges, depending on the nature of the target tissue, the bio-activity of the inventive compound and the use of any adjuvant or technique to obtain enhanced composition absorption. Such determinations are well within the normal skill in the art. For example, the concentration of the compound(s) used in practicing the instant invention can be about 0.1, 1, 2, 5, 10, 15, 20, 25, 50, 75, 100, 200, 500, or 1000 µg/mL.

The administration of the inventive compounds and associated compositions may be made to humans and animals, including all mammals (e.g., pigs, cows, horses, sheep, goats, mice, rats, cats, dogs, ferrets, primates). Application may also be made in combination with typical and/or experimental materials such as tissue grafts, tissue culture products, oxygen and dressings. In general, the composition can be administered topically, orally, transdermally, subcutaneously, intramuscularly, systemically, or by any other method known to those of skill in the art to be useful to deliver the inventive compounds to the target tissue. Compositions may also be applied in an in vitro or ex vivo manner, either to cells or patient grafts growing in culture, for example.

Due to their small size, the compounds of the invention are expected to be able to gain by themselves a level of permeability through the skin; however, certain techniques may be used to amplify this movement. For example, lipophilic (non-polar) side groups can be added to the compounds, or the compounds can be delivered to the skin in a lipophilic excipient, in order to enhance accessibility of the compound to the stratum corneum to allow translocation to the lower epidermal layers. In this manner such lipophilic modifications may be considered as having a pro-drug effect. Permeation enhancers such as known solvents and surfactants may be used in the excipient to allow better compound absorption. Special techniques that are useful in enhancing compound access to the targeted tissue/injury include, injection regimens, iontophoresis, electrophoresis and ultrasound. These treatments result in various effects (e.g., cavitation, mixing, increase in temperature) that may enhance permeation of the compounds in the skin or other target tissue.

Components that are typically incorporated into skin care preparations are well known in the art. Beside the bioactive compound component, compositions of the instant invention can contain other active agents such as niacinamide, phytantriol, farnesol, bisabolol and salicylic acid. Certain additional active agents act synergistically with the bioactive compound component, or enhance the shelf-life of the formulation.

Lipolytic agents can be included in compositions comprising a compound as described herein. Examples of lipolytic agents are carnitine, resveratrol, isoproterenol, aminophylline, theophylline, caffeine, xanthine derivatives, theobromine, forskolin, dibutyryl cyclic AMP, cyclic AMP phosphodiesterase inhibitors, epinephrine, catecholamines, niacinamide and pentoxifylline. Compositions of the invention can also comprise certain plant/vegetable extracts that are known to act as slimming agents. For instance, in U.S. Pat. No. 4,795,638 (herein incorporated by reference in its entirety) there is disclosed a thermo slimming cosmetic composition containing an oil-soluble plant extract having slimming action. Representative of these oil-soluble plant extracts are vegetable extracts including those of climbing ivy (*Hedera helix*), arnica (*Arnica montana*), rosemary (*Rosmarinus officinalis* N), marigold (*Calendula officinalis*), sage (*Salvia officinalis* N), ginseng (*Panax ginseng*), St. Johns wart (*Hypericum perforatum*), ruscus (*Ruscus aculeatus*), meadowsweet (*Filipendula ulmaria* L) and orthosiphon (*Ortosifon staminicus* Benth).

Lipolytic agents included in practicing the invention may be those that induce breakdown of lipid stores in adipocytes (i.e., fat cells) or other cells, or those that induce breakdown of lipids that are extracellular (i.e., not comprised in cellular fat stores). The total lipolytic activity of a compound of the invention and another lipolytic agent when in combination may be greater than their own respective activities when used separately from each other (i.e., synergy). Lipolysis can refer to the metabolism or breakdown of tri-, di-, and/or mono-glyceride to glycerol and free fatty acids. Also, lipolysis can encompass the breakdown of triglycerides to di- and/or mono-glycerides and free fatty acids.

Agents that exhibit a slimming effect on the skin, with or without lipolytic activity, may be included in practicing the invention. An example of such an agent is one that inhibits lipogenesis, thereby blocking fat deposition.

Where the composition is to be in contact with animal or human skin, additional components should be chosen that are suitable for application to keratinous tissue (i.e., stabile, low toxicity, hypoallergenic). The CTFA Cosmetic Ingredient Handbook, Second Edition (1992), which is herein incorporated by reference in its entirety, describes a wide variety of non-limiting cosmetic and pharmaceutical ingredients commonly used in the skin care industry that are suitable for use in the compositions of the present invention. Examples of these ingredient include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, benzoyl peroxide, erythromycin, zinc), anti-caking agents, antifoaming agents, antimicrobial agents (e.g., iodopropyl butylcarbamate), antioxidants, binders, biological additives, buffering agents, bulking agents, chelating agents, chemical additives, denaturants, external analgesics, polymers (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid [vitamin C], magnesium ascorbyl phosphate, ascorbyl glucosamine), skin-conditioning agents (e.g., humectants, including miscellaneous and occlusive), skin soothing and/or healing agents (e.g., panthenol and derivatives [e.g., ethyl panthenol], aloe vera, pantothenic acid and its derivatives, allantoin, bisabolol, dipotassium glycyrrhizinate), thickeners, particulate materials, structuring agents and vitamins. Many of these agents are described in detail in U.S. Pat. No. 6,492,326, which is herein incorporated by reference in its entirety, specifically with respect to the various ingredient descriptions.

The compositions of the present invention may contain a particulate material such as a metallic oxide. These particulates can be coated or uncoated, charged or uncharged. Non-limiting examples of particulate materials useful for preparing the instant invention include bismuth oxychloride, iron oxide, mica, mica treated with barium sulfate and $TiO_2$, silica, nylon, polyethylene, talc, styrene, polypropylene, ethylene/acrylic acid copolymer, sericite, aluminum oxide, silicone resin, barium sulfate, calcium carbonate, cellulose acetate, titanium dioxide, polymethyl methacrylate, and mixtures thereof. Inorganic particulate materials such as $TiO_2$, ZnO (zinc oxide), or $ZrO_2$ are commercially available from a number of sources. Particulate materials can be present in the composition at levels of from 0.01% to 2% by weight, or from 0.05% to 1.5% by weight, or from 0.1% to 1% by weight (all measures approximate).

The compositions of the present invention may contain a conditioning agent selected from humectants, moisturizers, or skin conditioners. A variety of these materials can be employed and each can be present at a level of from about 0.01% to 20%, or from about 0.1% to 10%, or from about 0.5% to 7% by weight of the composition (all measures approximate). These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, glycerin, hexanetriol, butanetriol, propylene glycol, butylene glycol and hexylene glycol; polyethylene glycols; sugars (e.g., melibiose) and starches; sugar and starch derivatives (e.g., alkoxylated glucose, fructose, glucosamine); hyaluronic acid; lactamide monoethanolamine; acetamide monoethanolamine; panthenol; allantoin; petroleum jelly; and mixtures thereof.

The compositions of the present invention can contain a structuring agent, which can be used for preparing a oil-in-water emulsion. Without being limited by any theory, it is believed that the structuring agent assists in providing rheological characteristics to the composition which contribute to the stability of the composition. For example, the structuring agent tends to assist in the formation of liquid crystalline gel network structures. The structuring agent may also function as an emulsifier or surfactant. The instant invention may contain from about 0.1% to 20%, from about 0.1% to 10%, or from about 0.5% to 9% of one or more structuring agents by weight of the composition (all measures approximate).

Structuring agents than can be incorporated in the present invention are selected from stearic acid, palmitic acid, stearyl alcohol, cetyl alcohol, behenyl alcohol, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. Other structuring agents that can be used in the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof.

Methods:

The instant invention is further directed to methods of using a compound described herein for treating the skin. Such treatment may be directed to the epidermis, dermis, or subcutaneous layer of the skin, for example. The purpose of such treatment can be to reduce the amount of subcutaneous fat or prevent the accumulation of subcutaneous fat. An example of treating the skin is administering a compound to skin over a subcutaneous layer that comprises a distribution of fat that is abnormal with respect to normal subcutaneous tissue. Another example of treating the skin is administering a compound to skin over a subcutaneous layer that is prone to developing a distribution of fat that is abnormal with respect to normal subcutaneous tissue. Cellulite (a.k.a. adiposis edematosa, dermopanniculosis deformans, status protrusus cutis, gynoid lipodystrophy) is an example of a skin condition that can be treated or prevented by these methods. Skin areas that are prone to developing cellulite for which the instant invention can be directed are the thighs, buttocks, pelvic region, lower limbs and abdomen, for example. While not being held to any particular theory, the compounds of the invention treat or prevent conditions of abnormal fat deposition/accumulation in the skin by (i) stimulating lipolysis in adipocytes, particularly those adipocytes of subcutaneous tissue, and/or by (ii) reducing or preventing adipogenesis in the subcutaneous tissue.

Methods of the invention are also directed to treating or preventing other conditions of abnormal fat deposition in the skin beside cellulite. For example, a compound can be used to treat or prevent lipedema, which is also known as painful fat syndrome. The invention can also be directed to treating or preventing lipomas or other fatty growths. The invention can also be directed to treating or preventing localized excess weight. The invention can also be directed to blocking or reducing lipogenesis or adipogenesis (i.e., promote anti-lipogenesis or anti-adipogenesis). An anti-adipogenesis feature of the invention is the ability to reduce the accumulation of lipids in the cytoplasm of adipocytes. As a result of this effect at the cellular level, another anti-adipogenesis feature of the invention is the ability to reduce adipose tissue growth or hypertrophy. Still another feature along these lines is the ability to block or reduce the differentiation of pre-adipocytes or fibroblasts to adipocytes. By "reducing," "inhibiting," "blocking," or "preventing" as referred to herein, it is meant that a compound brings down the occurrence, severity, size, volume, or associated symptoms of a condition or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, or 100% compared to how the condition would normally exist without application of the compound or composition comprising the compound.

Another embodiment of the invention is using a compound as described herein to stimulate lipolysis in cells such as adipocytes, particularly adipocytes in the skin or subcutaneous layer of the skin. Such a method is useful in treating or preventing (inhibiting) conditions such as cellulite. As referred to herein, stimulating, inducing, upregulating, elevating, or enhancing lipolysis in cells such as adipocytes means to increase the level of lipolysis in said cells over a basal level of lipolysis (e.g., resting state without added compound) or a level of lipolysis induced by non-active agents such as water. Such an increase would be by at least about 5%, 10%, 15%, 20%, 25%, 30%, 35%, 40%, 45%, 50%, 60%, 75%, 80%, 90%, 100%, 150%, 200%, 300%, 400%, 500%, 1000% or 10000%.

Skilled artisans would understand that, where treatment is ultimately directed the subcutaneous layer of the skin, formulations may be applied to the skin overlying the targeted subcutaneous region. Alternatively, methods such as mesotherapy which employ an injection regimen can be applied to directly place a therapeutic or cosmetic compound in the deeper layers of the skin such as the subcutaneous layer.

The compounds disclosed herein increase glycerol production by cells such as adipocytes. While not being held to any particular theory, this activity may be related to the lipolytic activity of the compounds, which stimulates the metabolism/breakdown of triglycerides (also di- and mono-glycerides) to free glycerol and free fatty acids. Certain embodiments of the invention are directed to increasing the glycerol production by adipocytes in the skin, particularly in the subcutaneous layer of the skin, by treatment of the skin with one or more compounds disclosed herein. The increase in glycerol production in the skin is beneficial given its moisturizing and protecting effects. This feature of the invention is an added benefit to the slimming and toning of the skin that occurs as a result of lipolysis of fat stores in the skin. Individuals with dry skin or easily irritated skin, for example, will benefit from the glycerol production effected by the invention, as will those seeking to maintain normal skin tone and smoothness.

It should be apparent that the disclosed methods can be used therapeutically or cosmetically. Regarding the latter use, the instant invention maintains normal, healthy skin traits, such as tone, elasticity, hydration, coloration, firmness and smoothness. All of these qualities can degrade with increased subcutaneous fat deposition.

While this disclosure is generally directed to describing the invention as being stimulatory to lipolysis in cells, it should also be understood that the invention inherently acts against lipogenesis, which process results in the production of fatty acid esterification to glycerol yielding tri-, di-, and mono-glycerides.

Tissues that can be targeted in practicing the instant invention are the skin and associated mucosal tissues of the skin. An associated mucosal tissue of the skin is any tissue organized in a manner similar to the skin, contains epithelial cells, and is directly continuous with the skin. Examples of such tissues are oral, nasopharyngeal, aural, anal and urogenital surfaces, as well as the palpebral conjunctiva of the eye. Other tissues that can be targeted in practicing the instant invention are those derived from the ectoderm, mesoderm and endoderm, or comprise epithelial cells, mesenchymal cells (e.g., fibroblasts), muscle cells, or nerve cells (e.g., neurons). Other organs, organ systems and tissues targeted by the invention are, for example, the circulatory system (e.g., heart, blood, blood vessels), digestive system (e.g., salivary glands, esophagus, stomach, liver, gallbladder, pancreas, small and large intestines, rectum), endocrine system (e.g., hypothalamus, pituitary gland, pineal gland, thyroid, parathyroids, adrenal glands), integumentary system (e.g., skin, hair, nails), lymphatic system (e.g., lymph nodes and vessels), immune system (e.g., tonsils, adenoids, thymus, spleen), muscular system (e.g., cardiac muscle, smooth muscle, skeletal muscle), nervous system (e.g., brain, spinal cord, peripheral nerves, nerves), reproductive system (e.g., ovaries, fallopian tubes, uterus, vagina, mammary glands, testes, vas deferens, seminal vesicles, prostate, penis), respiratory system (e.g., pharynx, larynx, trachea, bronchi, lungs, diaphragm), skeletal system (e.g., bones, cartilage, ligaments, tendons), and excretory system (e.g., kidneys, ureters, bladder, urethra). Certain embodiments of the invention are drawn to the application of a compound to one of the above tissues (e.g., skin) or cells (e.g., adipocyte, keratinocyte, epithelial cell, skin cell, fibroblast) in a manner that does not induce toxicity thereto.

The following examples are included to demonstrate certain embodiments of the invention.

EXAMPLES

Example 1

Synthesis of 4-methyl-2-(octanoylamino) Pentanoic Acid (HB2031)

Figure 2:
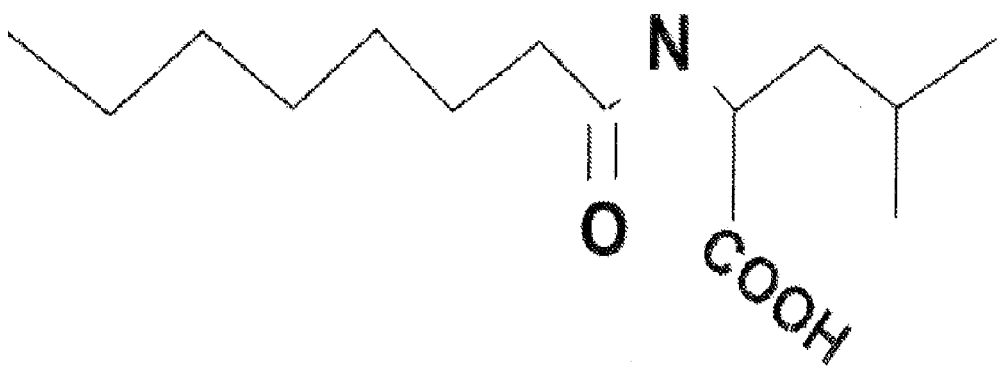
FIG. 2 shows the chemical formulae for (A) 4-methyl-2-(octanoylamino) pentanoic acid and (B) N-isopentyloctanamide. The structural and basic molecular formulae, as well as the molecular weight (MW), are additionally shown for each compound.
Figure 2:
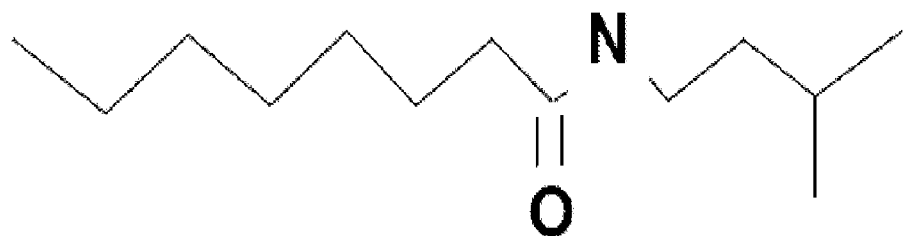

The following process was used to react leucine with octanoic acid to form 4-methyl-2-(octanoylamino) pentanoic acid, which is depicted in FIG. 2A. Fmoc-leucine-(Fmoc-2-Amino-4-methyl pentanoic acid)-Wang resin was stirred in 25% piperidine in dimethylformamide (DMF) for 20 minutes at room temperature. After being filtered and washed with DMF six times, the Kaiser test was found to be positive (ready for coupling). Coupling of octanoic acid was performed with three molar equivalents of the leucine resin amino groups followed by equal molar amounts to the octanoic acid of benzotriazol- 1-oxy-tris(pyrrolidino)phosphonium hexafluorophosphate (PyBop) and hydroxybenzotriazole hydrate (HOBt) of DMF. Upon the addition of 1.3 equivalents of diisopropylethyl amine (DIEA) to the other reagents in the reaction, it was stirred for 2 hours at room temperature. After the resin was filtered and washed three times with DMF and three times with DCM (dichloromethane) the Kaiser test was found to be negative, which is indicative of a complete reaction.

The dry resin was suspended in trifluoroacetic acid (TFA) and water (149:1) and stirred for 2 hours. The resin was filtered and then washed three times with TFA. The combined filtrates were roto-evaporated to remove the TFA. The product was dissolved in diethyl ether ($Et_2O$) and extracted three times with 5% acetic acid in water, water, saturated sodium bicarbonate in water, and with water. The $Et_2O$ phase was dried over anhydrous sodium sulfate, filtered and the sodium sulfate was wash three times with $Et_2O$. The combined filtrates were roto-evaporated to a solid.

Example 2

Synthesis of N-isopentyloctanamide (HB2032)

The following process was used to synthesize N-isopentyloctanamide (FIG. 2B), which is an analog of 4-methyl-2-(octanoylamino) pentanoic acid. Octanoic acid was combined with an equal molar amount of N-isopentylamine in DCM (dichloromethane) and stirred for five minutes. Benzotriazol-1-oxy-tris(pyrrolidino)phosphonium hexafluorophosphate (PyBop) and hydroxybenzotriazole hydrate (HOBt) equivalent to the molar amounts of the first two components was added followed by 1.3 equivalents of diisopropylethyl amine (DIEA) and the reaction was stirred for 2 hours at room temperature. The solution was extracted three times with 5% acetic acid in water, water, saturated sodium bicarbonate in water and with water. The DCM phase was dried over anhydrous sodium sulfate, filtered, and the sodium sulfate was washed three times with DCM. The combined filtrates were roto-evaporated to an oil.

Example 3

Figure 3:
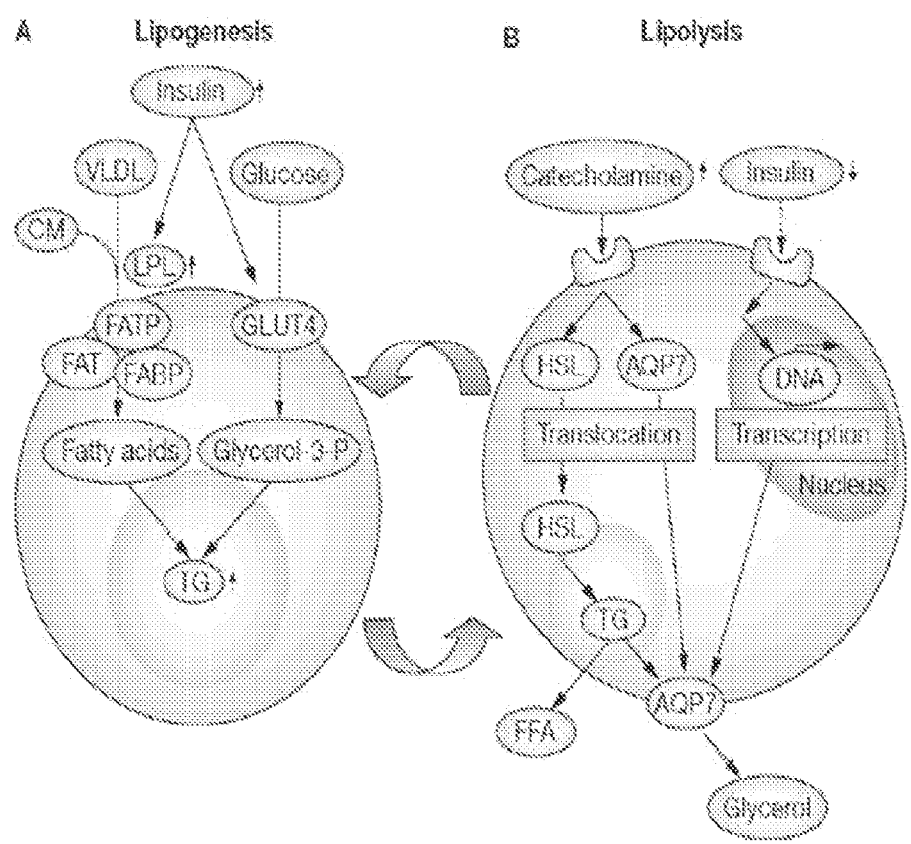
FIG. 3 shows certain signaling pathways in adipocytes underlying (A) lipogenesis and (B) lipolysis. LDL, low-density lipoprotein; VLDL, very low-density lipoprotein; TG, triglyceride; FFA, free fatty acid; HSL, hormone-sensitive lipase; AQP7, aquaporin-7.

Measuring Effects of 4-methyl-2-(octanoylamino) Pentanoic Acid and N-isopentyloctanamide on Lipolysis and Adipogenesis Lipolysis:

As shown in FIG. 3, both free fatty acids and glycerol are the products of lipolysis and thus measurement of free fatty acid release directly correlates with the degree of lipolytic activity in adipocytes. The degree of fatty acid release can be used to gauge the relative level of glycerol release given this correlation. The following methods were used to determine the effect of 4-methyl-2-(octanoylamino) pentanoic acid and N-isopentyloctanamide on lipolysis in adipocytes.

The induction of lipolysis in differentiated adipocytes was determined in 3T3-L1 adipocytes using a fatty acid assay kit manufactured by BioVision (Mountain View, Calif.) (Free Fatty Acid Quantification Kit, Cat. No. K612-100). Free fatty acid release correlates with an increase in the level of glycerol. Adipocytes for these assays were prepared as follows. 3T3-L1 murine pre-adipocytes were purchased from the American Type Culture Collection (ATCC) (CL-173™). The cells were cultured in complete medium (ATCC-formulated Dulbecco's Modified Eagle's Medium supplemented with 10% bovine calf serum) and allowed to reach 100% confluence. The induction of differentiation or adipogenesis was carried out in complete medium. On day 0, cells were treated with complete medium containing induction agents (100 μg/ml isobutylmethyxanthine (Sigma, St. Louis, Mo.), 5 μg/ml insulin and 2 μg/ml dexamethasone). On day 3, cells were changed to complete medium containing 5 μg/ml insulin and incubated for 2-3 days. Then, cells were maintained in complete medium for 3-6 days when the majority of cells developed observable intracellular lipid droplets.

For analyzing the effects of 4-methyl-2-(octanoylamino) pentanoic acid and N-isopentyloctanamide on lipolysis, cells (adipocytes prepared above) were treated with either of these compounds at 100 μg/ml. Alternatively, cells were treated overnight with certain substances (e.g., resveratrol, isoproterenol, aminophylline, theophylline) (100 μg/ml) previously known to be lipolysis inducers. Supernatant from each of the cultures was measured for relative glycerol release as estimated using the free fatty acid quantification kit from BioVision following the manufacturer's instructions.

Figure 4:
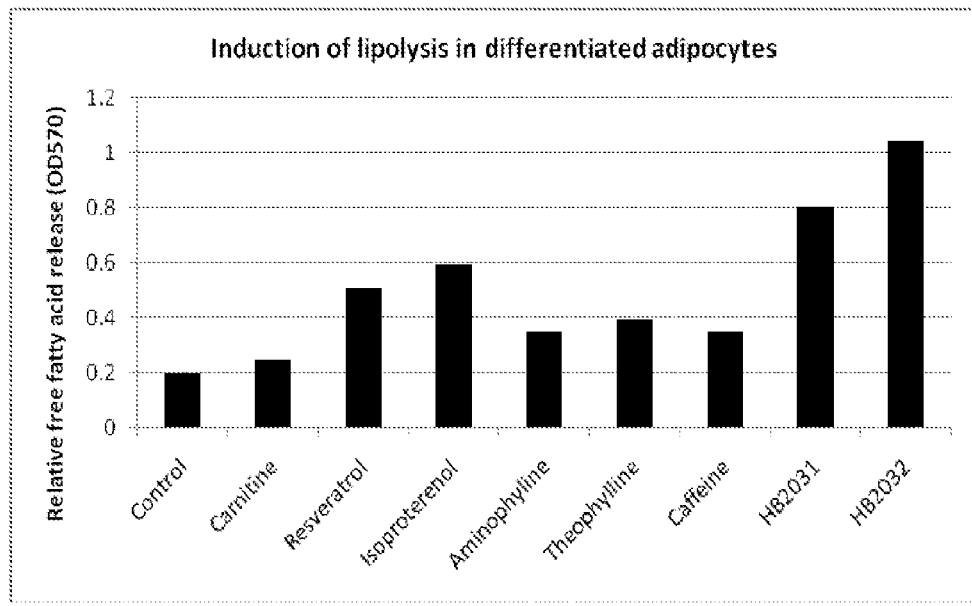
FIG. 4 shows relative free fatty acids production in 3T3-L1 adipocytes that had been exposed overnight to 100 μg/ml of carnitine, resveratrol, isoproterenol, aminophylline, theophylline, caffeine, 4-methyl-2-(octanoylamino) pentanoic acid (HB2031), or N-isopentyloctanamide (HB2032). Phosphate-buffered salt (PBS) was used in the control sample.
Figure 5:
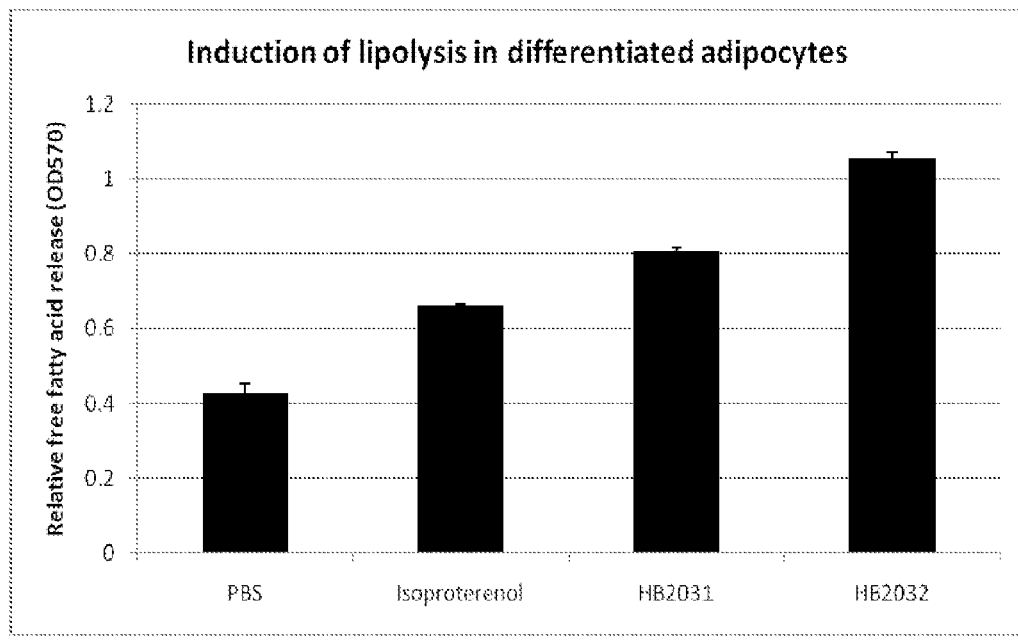
FIG. 5 shows relative free fatty acids production in 3T3-L1 adipocytes that had been exposed overnight to 100 μg/ml of isoproterenol, 4-methyl-2-(octanoylamino) pentanoic acid (HB2031), or N-isopentyloctanamide (HB2032). PBS was used in the control sample.

FIG. 4 shows that 4-methyl-2-(octanoylamino) pentanoic acid (HB2031) and N-isopentyloctanamide (HB2032) induced free fatty acids production in adipocytes (as determined by measuring free fatty acid production) to a higher degree than all the other compounds tested including isoproterenol, aminophylline and theophylline. When the above assay was performed in triplicate with isoproterenol, HB2031 and HB2032, the latter two compounds were shown to be significantly more active than isoproterenol (FIG. 5). Both HB2031 and HB2032 were not cytotoxic to 3T3-L1 adipocytes at the concentrations used to simulate lipolysis (data not shown).

Adipogenesis:

Intracellular lipid droplet production in adipocytes is a feature of adipogenesis. Therefore, adipogenesis was monitored by staining for lipid droplets in cells using the Adipogenesis Assay Kit from Cayman (Ann Arbor, Mich.) following the manufacture's instructions. This assay stains cellular lipids with Oil red O dye.

Figure 6:
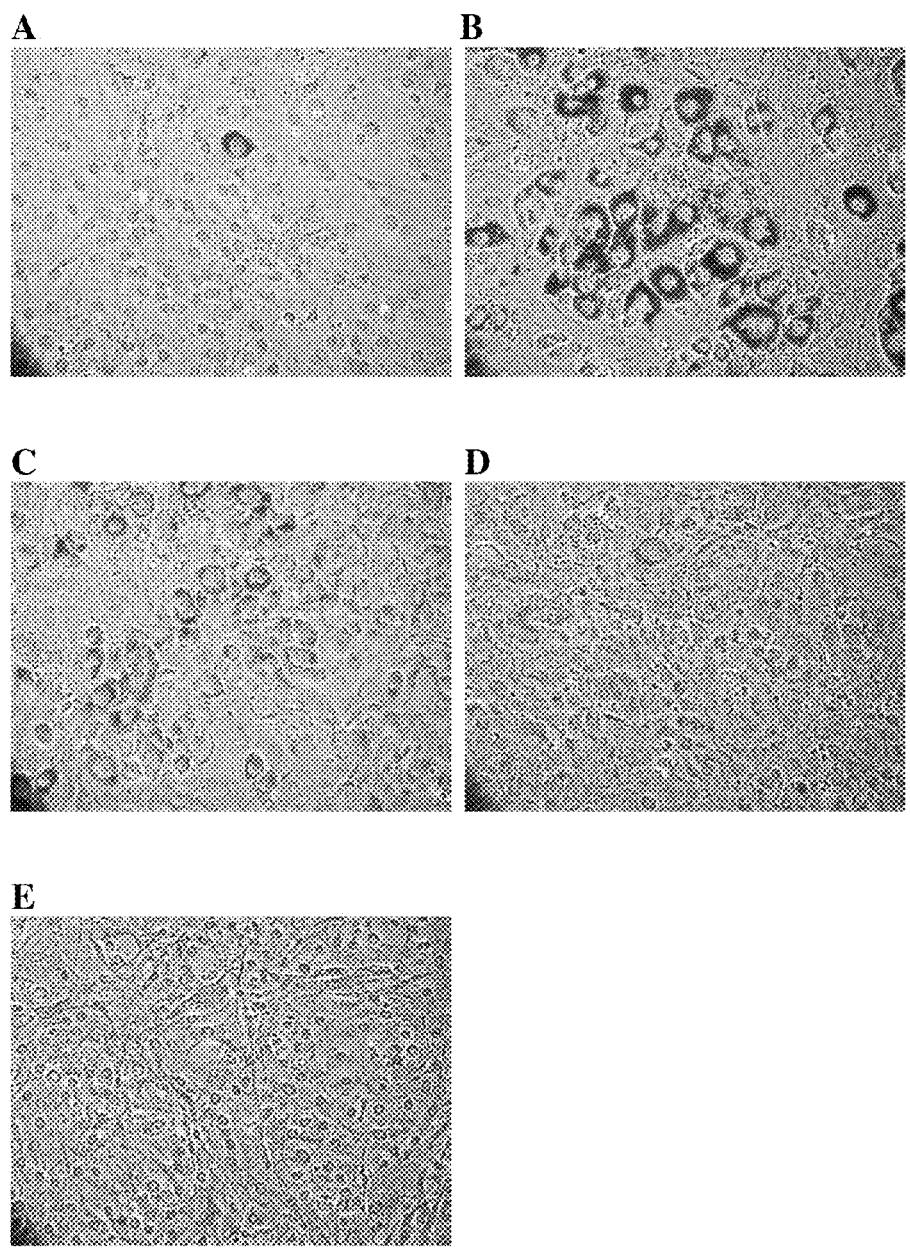
FIG. 6 shows the anti-adipogenesis activity of N-isopentyloctanamide (HB2032). A) 3T3-L1 preadipocytes grown in complete medium without addition of adipogenesis-inducing agents. B) 3T3-L1 preadipocytes were induced to fully differentiated adipocytes after nine days of induction with adipogenesis inducers. C) Cells treated with 100 μg/ml of HB2032 in the presence of adipogenesis inducers for nine days. D) Cells treated with 150 μg/ml of HB2032 in the presence of adipogenesis inducers for nine days. E) Cells treated with 200 μg/ml of HB2032 in the presence of adipogenesis inducers for 9 days. Cells are stained for lipid content with Oil red O dye. Images are as shown under a dissecting microscope.

To analyze the effects of 4-methyl-2-(octanoylamino) pentanoic acid and N-isopentyloctanamide on adipogenesis, these compounds were individually added to a cell culture when adipogenesis was induced (day 0) (refer to above protocol) and maintained in the culture during the entire differentiation process. The positive control in this assay for adipocyte formation was a cell culture that had been induced to undergo differentiation from pre-adipocyte to adipocyte without the addition of a test compound (FIG. 6B). After a 7-day induction period, 50-70% of cells in the positive control became fully differentiated with visible accumulation of multiple cytoplasmic lipid droplets as viewed under a dissecting microscope. The negative control was a cell culture that was incubated in complete medium without adipogenesis induction agents (FIG. 6A).

N-isopentyloctanamide (HB2032) inhibited the differentiation of cells into adipocytes by slowing down the formation of enlarged cells as well as the accumulation of intracellular lipid droplets. These effects were observed in a concentration dependent manner (FIGS. 6C, D, E) (refer to figure legend) and in comparison to the positive control for adipocyte induction (FIG. 6B). Of the cells that were treated with a low concentration of HB2032 (e.g., FIG. 6C), a significant number became differentiated; however the intensity of cellular lipid formation was significantly reduced as indicated by reduced Oil red O staining.

Example 4

Figure 7:
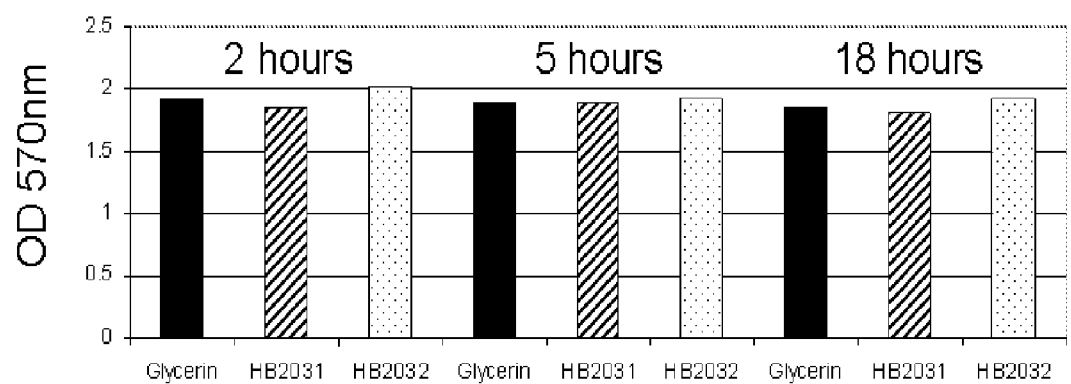
FIG. 7 shows the effects of 100 μg/ml of 4-methyl-2-(octanoylamino) pentanoic acid (HB2031) and N-isopentyloctanamide (HB2032) on skin viability using the Epi-Derm™ Skin Model (MatTek, MA) in combination with a modified MTT assay, after 2, 5 and 18 hour incubation periods. Glycerin treatment was used as a control.

Measuring Cytotoxicity Levels of 4-methyl-2-(octanoylamino) Pentanoic Acid and N-isopentyloctanamide The EpiDerm™ MTT assay (MatTek, Ashland, Mass.) was used to determine whether 4-methyl-2-(octanoylamino) pentanoic acid (HB2031) and N-isopentyloctanamide (HB2032) exhibit any level of cytotoxicity toward skin tissue. The EpiDerm™ Skin Model consists of organized basal, spinous, granular, and cornified layers analogous to those found in vivo and exhibits in vivo-like morphological and growth characteristics which are uniform and highly reproducible. As shown in FIG. 7, there was no difference in cell viability (determined by $OD_{570mm}$) between treatments with HB2031 or HB2032 compared to the glycerin vehicle. Both compounds also showed no toxicity to the same skin tissue when treated at 1 mg/ml for 24 hours (data not shown).

All of the compositions or methods disclosed and claimed herein can be made and executed without undue experimentation in light of the present disclosure. While the compositions and methods of this invention have been described in terms of certain embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention.

All patents and publications identified in this application are hereby incorporated by reference in their entirety.

What is claimed is:

1. A method of stimulating lipolysis in one or more adipocytes of a mammal, said method comprising administering to the skin tissue of said mammal a composition comprising a pharmaceutically acceptable carrier and a pharmaceutically effective amount of a compound, or salt thereof, wherein the compound is:

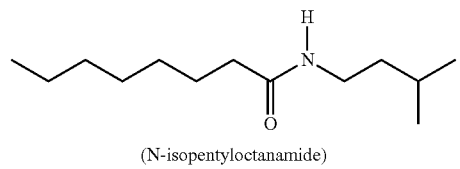

(N-isopentyloctanamide)

2. The method of claim 1, wherein said composition further comprises carnitine, resveratrol, isoproterenol, aminophylline, theophylline, or caffeine.

3. The method of claim 1, wherein said composition is administered to skin tissue superficial to the subcutaneous layer.

4. The method of claim 1, wherein said composition is directly injected into the subcutaneous layer of the skin tissue.

5. A method of stimulating lipolysis in one or more adipocytes of a mammal, said method comprising administering to the skin tissue of said mammal a composition comprising a pharmaceutically acceptable carrier and a pharmaceutically effective amount of a compound or pharmaceutically acceptable salts thereof, wherein the compound is of the formula:

$R_1$—CO—NH—$R_2$; wherein $R_1$ is a saturated or unsaturated aliphatic chain of 5 to 9 carbon atoms, $R_2$ is an alkyl of 5 to 9 carbon atoms, and wherein the $R_1$—C(O) portion of the formula is a fatty acyl group.

6. The method of claim 5, wherein the fatty acyl group is an octanoyl group.

7. The method of claim , wherein the fatty acyl group is saturated.

8. The method of claim 5, wherein said composition is in the form of an aerosol, emulsion, liquid, lotion, cream, paste, ointment, powder, or foam.

9. The method of claim 5, wherein said composition further comprises carnitine, resveratrol, isoproterenol, aminophylline, theophylline, or caffeine.

10. The method of claim 5, wherein said composition is administered to skin tissue superficial to the subcutaneous layer or directly injected into the subcutaneous layer.

11. A method of reducing adipogenesis in subcutaneous tissue of a mammal, said method comprising administering to the skin tissue of said mammal a composition comprising a pharmaceutically acceptable carrier and a pharmaceutically effective amount of a compound, or salt thereof, wherein the compound is:

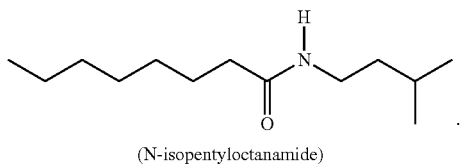

(N-isopentyloctanamide)

12. The method of claim 11, wherein said composition further comprises carnitine, resveratrol, isoproterenol, aminophylline, theophylline, or caffeine.

13. The method of claim 11, wherein said composition is administered to skin tissue superficial to the subcutaneous layer.

14. The method of claim 11, wherein said composition is directly injected into the subcutaneous layer of the skin tissue.

15. A method of reducing adipogenesis in subcutaneous tissue of a mammal, said method comprising administering to the skin tissue of said mammal a composition comprising a pharmaceutically acceptable carrier and a pharmaceutically effective amount of a compound or pharmaceutically acceptable salts thereof, wherein the compound is of the formula:

$R_1$—CO—NH—$R_2$; wherein $R_1$ is a saturated or unsaturated aliphatic chain of 5 to 9 carbon atoms, $R_2$ is an alkyl of 5 to 9 carbon atoms, and wherein the $R_1$—C(O) portion of the formula is a fatty acyl group.

16. The method of claim 15, wherein the fatty acyl group is an octanoyl group.

17. The method of claim 15, wherein the fatty acyl group is saturated.

18. The method of claim 15, wherein said composition is in the form of an aerosol, emulsion, liquid, lotion, cream, paste, ointment, powder, or foam.

19. The method of claim 15, wherein said composition further comprises carnitine, resveratrol, isoproterenol, aminophylline, theophylline, or caffeine.

20. The method of claim 15, wherein said composition is administered to skin tissue superficial to the subcutaneous layer or directly injected into the subcutaneous layer.

* * * * *

UNITED STATES PATENT AND TRADEMARK OFFICE
CERTIFICATE OF CORRECTION

PATENT NO. : 9,511,042 B2  
APPLICATION NO. : 13/703292  
DATED : December 6, 2016  
INVENTOR(S) : Timothy J. Falla et al.

Page 1 of 1

It is certified that error appears in the above-identified patent and that said Letters Patent is hereby corrected as shown below:

In the Claims

In Column 18, Line 54 for Claim 7, insert -- In the method of claim 5, wherein --, therefore.

Signed and Sealed this
Twenty-eighth Day of February, 2017

Michelle K. Lee
*Director of the United States Patent and Trademark Office*